United States Patent
Giunta et al.

(10) Patent No.: US 9,897,243 B2
(45) Date of Patent: Feb. 20, 2018

(54) METHOD AND SYSTEM FOR THE REMOTE DETECTION OF THE POSITION OF A PIG DEVICE INSIDE A PRESSURIZED PIPELINE

(71) Applicant: ENI S.p.A., Rome (IT)

(72) Inventors: Giuseppe Giunta, San Donato Milanese (IT); Giancarlo Bernasconi, Malnate (IT)

(73) Assignee: ENI S.p.A., Rome (IT)

(*) Notice: Subject to any disclaimer, the term of this patent is extended or adjusted under 35 U.S.C. 154(b) by 311 days.

(21) Appl. No.: 14/652,245

(22) PCT Filed: Dec. 12, 2013

(86) PCT No.: PCT/EP2013/076413
§ 371 (c)(1),
(2) Date: Jun. 15, 2015

(87) PCT Pub. No.: WO2014/095581
PCT Pub. Date: Jun. 26, 2014

(65) Prior Publication Data
US 2015/0323119 A1      Nov. 12, 2015

(30) Foreign Application Priority Data
Dec. 20, 2012   (IT) .............................. MI2012A2196

(51) Int. Cl.
*F16L 55/48*    (2006.01)
*G01N 29/07*    (2006.01)
(Continued)

(52) U.S. Cl.
CPC .............. *F16L 55/48* (2013.01); *G01N 29/07* (2013.01); *G01S 11/14* (2013.01); *G01N 2291/011* (2013.01); *G01V 1/001* (2013.01)

(58) Field of Classification Search
None
See application file for complete search history.

(56) References Cited

U.S. PATENT DOCUMENTS 3,916,699 A * 11/1975 Moran ................... G01N 29/14
73/592
5,417,112 A *  5/1995 Rosenberg ............. G01B 7/003
324/207.22
(Continued)

FOREIGN PATENT DOCUMENTS

WO   WO 2009/067769 A1    6/2009
WO   WO 2009067769 A1 *   6/2009  ............... F17D 3/08
(Continued)

OTHER PUBLICATIONS

U.S. Appl. No. 14/711,885, filed May 14, 2015, Giunta, et al.
International Search Report and Written Opinion dated Jan. 22, 2014 in PCT/EP2013/076413.

*Primary Examiner* — Paul West
*Assistant Examiner* — Mark A Shabman
(74) *Attorney, Agent, or Firm* — Oblon, McClelland, Maier & Neustadt, L.L.P.

(57) ABSTRACT

A method and a system remotely detect the position of a pig device inside a pipeline for transporting pressurized fluids, like for example long distance oil and gas pipelines having a strategic international value. The method foresees equipping the pipeline with pressure sensors in contact with the fluid, located at at least one of the two terminals of the pipeline, and the sending and processing of signals by a control unit. The operation of the system is that of identifying and locating, in real time and continuously, a pig device that moves intermittently inside the pipeline, for example during cleaning, monitoring, measurement and non-destructive control operations.

14 Claims, 3 Drawing Sheets

Figure 1:
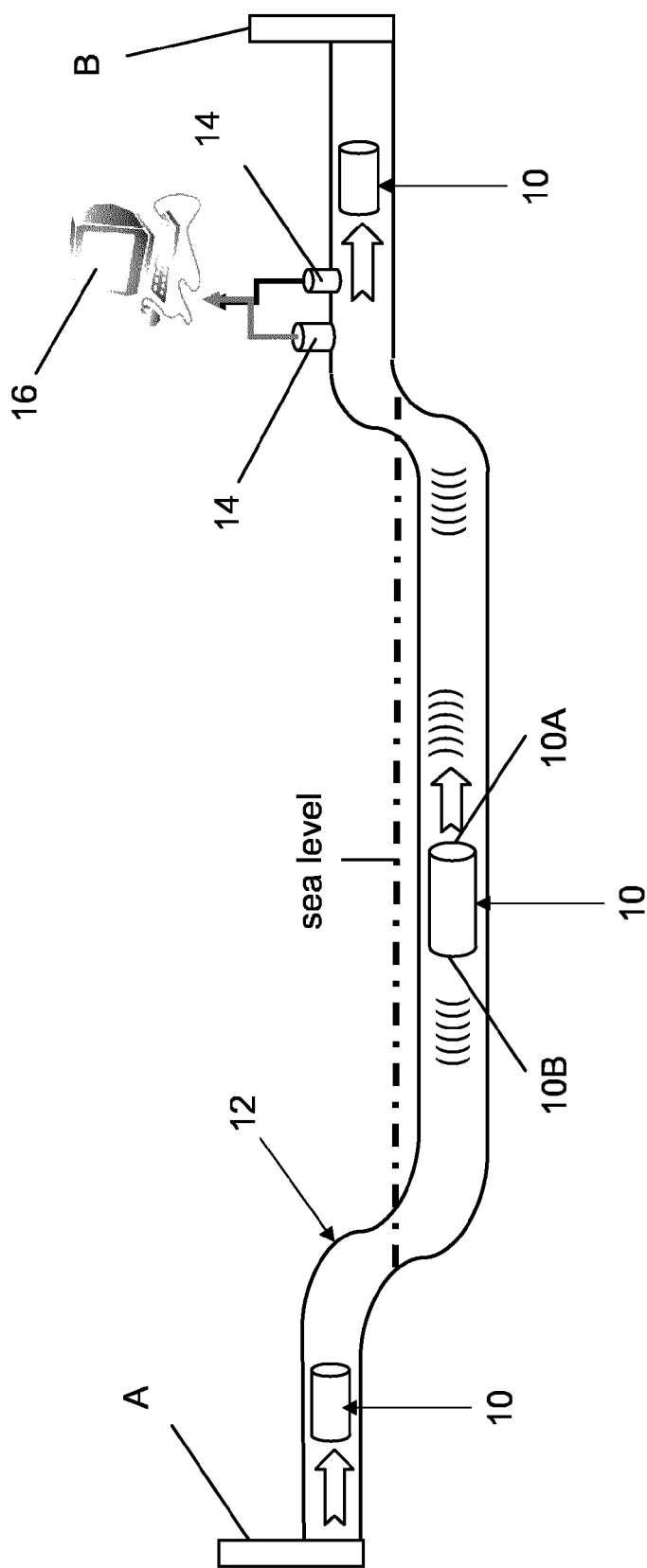

(51) Int. Cl.
 *G01S 11/14* (2006.01)
 *G01V 1/00* (2006.01)

(56) References Cited

U.S. PATENT DOCUMENTS

| | | | | |
|---|---|---|---|---|
| 5,549,000 | A * | 8/1996 | Brown | G01V 1/001 |
| | | | | 73/587 |
| 7,886,604 | B2 * | 2/2011 | Hirao | G01N 29/2412 |
| | | | | 73/623 |
| 9,599,272 | B2 * | 3/2017 | Hartog | F16L 55/48 |
| 2002/0097058 | A1 * | 7/2002 | Borghi | G01S 13/84 |
| | | | | 324/644 |
| 2009/0085582 | A1 * | 4/2009 | Sinha | F16L 55/48 |
| | | | | 324/644 |
| 2010/0283543 | A1 | 11/2010 | Shivaram et al. | |
| 2011/0103189 | A1 | 5/2011 | Paulson | |
| 2011/0139538 | A1 * | 6/2011 | Hill | F17D 5/06 |
| | | | | 181/123 |
| 2011/0149688 | A1 | 6/2011 | Hill et al. | |
| 2012/0137781 | A1 | 6/2012 | Hill et al. | |
| 2012/0243376 | A1 | 9/2012 | Dalmazzone et al. | |
| 2013/0214771 | A1 * | 8/2013 | Tiernan | G01N 33/383 |
| | | | | 324/242 |

FOREIGN PATENT DOCUMENTS

| | | |
|---|---|---|
| WO | WO 2009/155708 A1 | 12/2009 |
| WO | WO 2010/020781 A1 | 2/2010 |
| WO | WO 2011/039589 A1 | 4/2011 |

* cited by examiner

METHOD AND SYSTEM FOR THE REMOTE DETECTION OF THE POSITION OF A PIG DEVICE INSIDE A PRESSURIZED PIPELINE

The present invention refers to a method and to a system for the remote detection of the position of a pig device inside pipelines for transporting fluids at high pressure, like for example long distance oil and gas pipelines that have a strategic international value.

In order to monitor, inspect and/or clean the pipes for transporting fluids, it is generally known to use devices commonly called "pigs". Such devices normally comprise pipeline inspection gauges (pigs) that are inserted in the pipeline and that move adhering to the walls of the pipeline itself. The pig devices can be pushed by a liquid or by a gas that is specially injected in the pipeline, or they can be more commonly transported by the fluid in regular transit inside the pipeline itself.

Some of these devices are used to remove deposits inside the pipeline, others contain measuring instrumentation that carries out the scanning of the inner surface and of the thickness of the pipes, and others collect objects and/or dusts that have been dispersed inside the pipeline. In all cases it is extremely important to know the position of the pig device and to know whether it has possibly been stuck inside the pipeline.

To this day there are already various systems for locating and/or tracking a pig device inside a generic pipeline. For example, a conventional system monitors the pressure and the volume of fluids upstream and downstream of the pig device so as to evaluate its position inside the pipeline.

Other systems propose a more accurate location through the measurement of the vibrations produced by the pig device during its movement, also by mounting active sources of electromagnetic or sound waves on the pig device itself. As an example, document EP 0122704 A2 describes a system for detecting a pig device inside a pipe that uses geophones installed near to the pipe itself. Geophones are capable of detecting the vibrations caused by the pig device during its passage through variations of the inner section of the pipe (welding, valves, etc.).

Documents EP 1042691 A2 and U.S. Pat. No. 5,461,354 A describe systems that use a network of magnetic sensors arranged along the pipeline to detect the passage of the pig device that, in turn, is provided with devices inside it that are capable of communicating with such sensors.

Document WO 2009/067769 A1 describes a network of sound sensors arranged along the pipeline, as well as a corresponding apparatus for generating acoustic transients positioned on the pig device.

Document WO 2010/020781 A1 describes the use of an optical fibre that is positioned along the pipe. The optical fibre acts as a DAS (Distributed Acoustic Sensing) system for detecting the vibrations generated by the passage of the pig device.

Finally, there are other methods that are used to locate a pig device that is stuck in a pipeline, for example generating suitable hydraulic transients and measuring the return times of the echoes that are generated on the blocked pig device.

In general, therefore, most known systems that locate and/or follow a pig device inside a pipeline operate through measuring and processing the signals collected by a plurality of sensors arranged along the pipeline itself. Such known systems however have a series of drawbacks.

A first drawback is due to the fact that the aforementioned locating and/or following systems require numerous measurement stations to be placed along the pipeline in order to obtain good accuracy in identifying the position of the pig device. It can however be costly and complicated to provide such measurement stations, in particular in deep offshore or underground pipes.

Another drawback is due to the fact that the majority of locating and/or tracking systems of the known type use passive measurements, like for example the vibrations generated by the pig device during its movement. It is therefore clear how such locating and/or tracking systems do not work when the pig device is blocked inside the respective pipe.

Some locating and/or tracking systems of the known type finally need an active source on board of the pig device. In other words, special pig devices must be used that are provided on the inside with suitable measurement and control equipment, with consequent increase in the costs and in the constructive complexity.

The purpose of the present invention is therefore that of making a method and a system for the remote detection of the position of a pig device inside pipelines for transporting pressurised fluids that are capable of solving the drawbacks mentioned above with reference to the prior art in an extremely simple, cost-effective and particularly functional manner.

In detail, one purpose of the present invention is that of making a method and a system for remotely detecting the position of a pig device inside pipelines that do not require, along the pipeline, complex and costly measurement stations to be installed.

Another purpose of the present invention is to provide a method and a system for the remote detection of the position of a pig device inside pipelines that do not require special pig devices to be used equipped to communicate with possible measurement stations positioned outside the pipeline.

A further purpose of the present invention is that of making a method and a system for the remote detection of the position of a pig device inside pipelines that are capable of effectively identifying the position of such a pig device both when the pig device itself is moving and when it is stopped.

These purposes according to the present invention are achieved by making a method and a system for the remote detection of the position of a pig device inside pipelines for transporting pressurised fluids as outlined in the independent claims.

Further characteristics of the invention are highlighted by the dependent claims, that are an integrating part of the present description.

In general, the method and the system according to the present invention relate to situations in which the pig device advances in the pipe with an intermittent movement, with alternating advance and stop phases of a few minutes, and it uses the principles of the prior art in combination. Sound sensors, positioned at at least one end of the pipeline, measure the sound signals produced by the pig device during its movement, as occurs in the prior art.

At the moment in which it stops the pig device generates a hydraulic transient, which can be considered like a water hammer, that reverberates on both the end terminals of the pipe. Therefore, on the two end terminals of the pipeline, stationary waves are generated, the periods of which are proportional to the distance of the pig device from the measuring point. A special control unit, which is operatively remotely connected to the sound sensors, is thus used to measure the hydraulic transients produced by the stoppage of the pig device, so as to obtain its position inside the pipe.

Figure 2A:
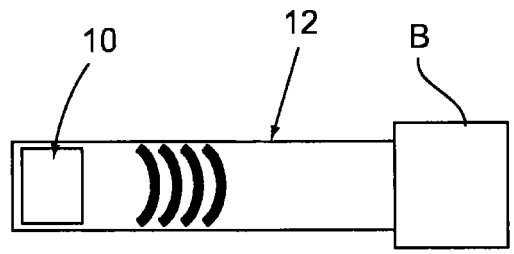
Figure 2A:
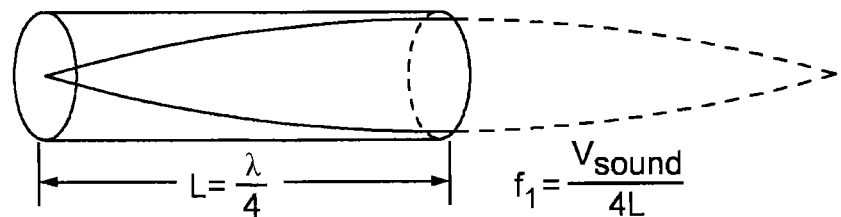
Figure 2A:
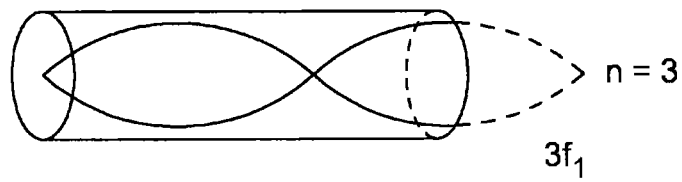
Figure 2A:
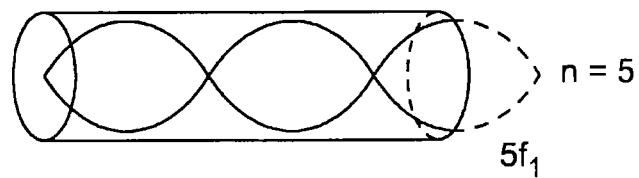
Figure 2B:
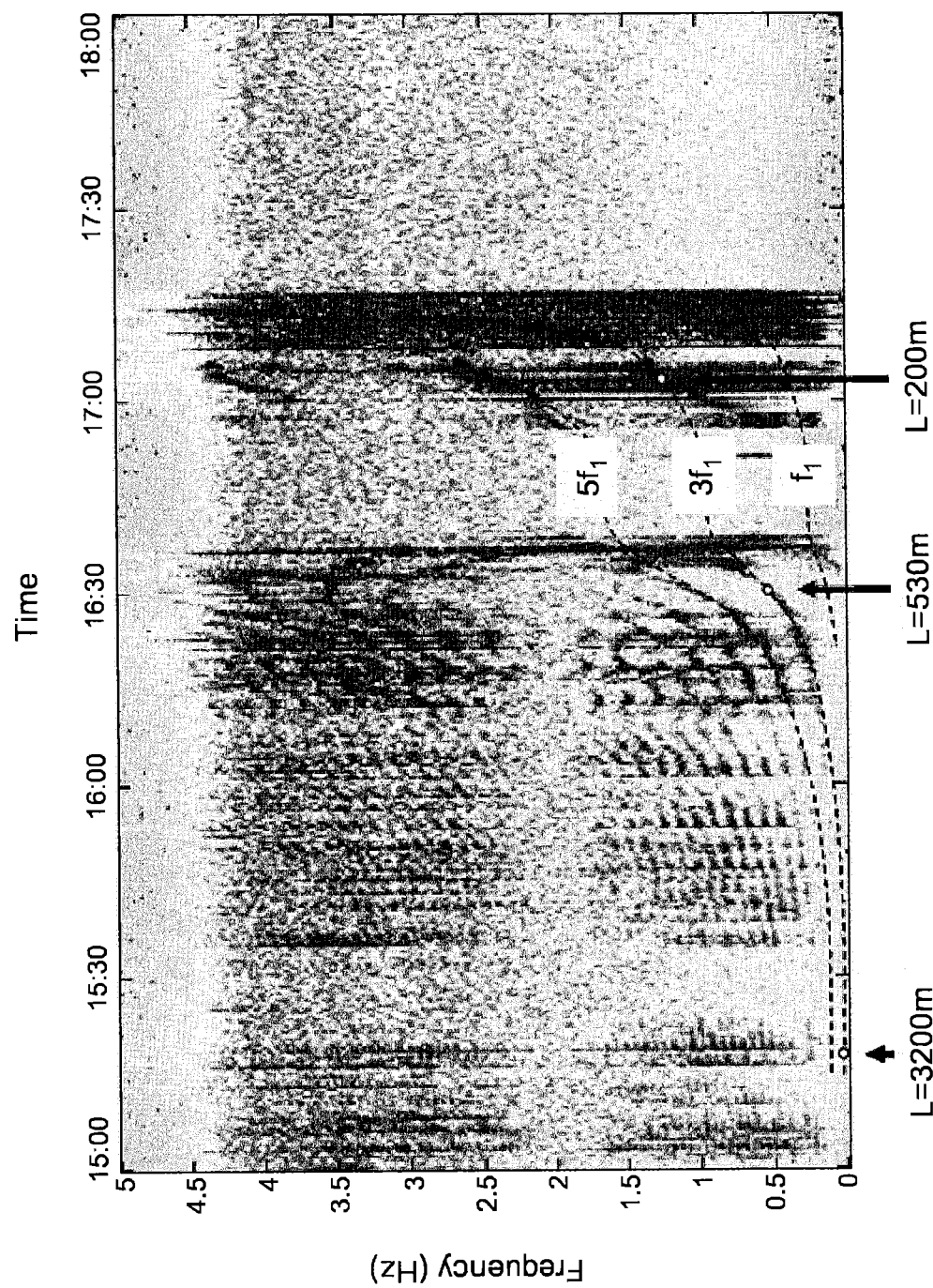

The characteristics and the advantages of a method and of a system for the remote detection of the position of a pig device inside pipelines for transporting pressurised fluids according to the present invention shall become clearer from the following description, given as an example and not for limiting purposes, with reference to the attached schematic drawings, in which:

FIG. 1 is a schematic view illustrating the application of the method and of the system for the remote detection of the position of a pig device to a generic underwater pipeline for transporting gas, with the launching of the pig device from a starting terminal A (pumping station) and the collection of the pig device itself in an arrival terminal B;

FIG. 2A schematically illustrates three distinct graphical interpretations of the spectral peaks of the resonance harmonics of three different sound pressure signals measured by the arrival terminal B of the pig device; and FIG. 2B shows a spectrogram of the three different sound pressure signals of FIG. 2A.

With reference to the figures, these show a method and a system for remotely monitoring the position of a pig device according to the present invention. The pig device, wholly indicated with reference numeral 10, is configured so as to move inside a generic pipeline 12 due to the pressure of the fluid transported by the pipeline 12 itself. The fluid can be made up, for example, of natural gas.

The method and the system according to the present invention are capable of effectively detecting the position of the pig device 10 when it moves inside the pipeline 12 with alternating advance and stoppage phases. These alternating advance and stoppage conditions occur, for example, in the pigging phases of the pipeline 12 when the fluid is transported at low pressure and/or when the differential pressure between the two front 10A and rear 10B sides of the pig device 10 is not particularly high.

In the practical embodiment of the method and of the system according to the present invention, illustrated in FIGS. 2A and 2B and described more in detail in the rest of the description, a pressure equal to around 8 bar on the rear thrust side 10B and equal to around 5 bar on the front advancing side 10A of the pig device 10 was measured, with a differential pressure equal to around 3 bar. Typically, the movement of the pig device 10 with alternating advance and stoppage phases occurs with absolute pressure of the fluid that is lower than 10 bar and with a differential pressure of between 1 bar and 3 bar between the two front 10A and rear 10B sides of the pig device 10 itself. The absolute and differential pressure values, which determine an intermittent advancement of the pig device 10 also depend upon the degree of internal corrosion/roughness of the pipeline 12 and upon the type of pig device 10 used.

In general, when the thrust force on the pig device exceeds the force due to static friction on the inner walls of the pipeline 12, the pig device 10 itself starts to move, generating, in normal operating conditions, a constant movement of fluid. When the pressure of the fluid in the pipeline 12 is particularly low, and/or if the pumping of such a fluid is insufficient, the pressure on the rear thrusting side 10B decreases and the pig device 10 again stops after a certain time period, causing there to be a sudden depression on the front side 10A and a just as sudden compression on the rear thrusting side 10B, which is similar to a hydraulic "water hammer". These two hydraulic transients, due to the pressure variations that arise at the front 10A and rear 10B sides of the pig device 10, propagate in an opposite direction in the pipeline 12 like sound waves confined in the pipeline 12 itself.

The system for the remote detection of the position of the pig device 10 therefore foresees the installation of one or more sensors 14, like for example hydrophones or vibro-acoustic sensors, in special measurement stations arranged at at least one end of the pipeline 12. The opposite inlet and outlet ends of the pipeline 12 are identified respectively with the starting terminal A (pumping station) and the arrival terminal B (collection station) of the pig device 10.

The vibro-acoustic sensors 14 detect the sound waves corresponding to the aforementioned hydraulic transients. The vibro-acoustic sensors 14 are operatively connected, through a suitable wired or wireless type communication system, to a control unit 16 that performs the measurement of the arrival times of the signals coming from the sound waves.

From the analysis of the arrival sound signals recorded at the two terminals A and B of the pipeline 12, being known the propagation speed of the hydraulic transients, that can be found with mathematical sound propagation models which take into consideration the physical and geometrical characteristics of the system consisting of the pipeline 12, of the fluid transported and of the external medium that surrounds such a pipeline 12, it is possible to calculate the position of the pig device 10 along the pipeline 12. By "external medium" we mean to indicate the environment (soil or water) that surrounds the pipeline 12. The propagation parameters of the sounds inside the pipeline 12 substantially depend upon the external medium in the case in which liquid is transported, whereas in the case in which gas is transported, the external medium has a considerably smaller influence.

The two terminals A and B of the pipeline 12, due to the presence of the regulation apparatuses of the flow of fluid inside the pipeline 12 itself, behave like physical mismatches with respect to the propagation of sound waves. The sound waves generated by the stoppage and the restarting of the pig device 10 therefore, remain trapped in the portion of pipeline 12 comprised between the same pig device 10 and the apparatuses for regulating the flow of fluid positioned at the ends of the pipeline 12.

The reverberations of the sound waves that are generated inside the two pipeline sections 12 positioned upstream and downstream of the pig device 10, respectively, generate stationary waves. The reverberation period or, in an equivalent manner, the resonance frequencies of such stationary waves, which are generally different on the two sides of the pig device 10, are a function of the length of the free section and of the propagation speed of the sound wave in the pipeline 12.

With the establishing of the stationary waves in the pipeline 12, caused by the stoppage of the pig device 10, it is possible to calculate the distance of such a pig device 10 from the recording point, through the measurement of the acoustic resonance frequencies and/or reverberation period of these stationary waves, also from a single side of the pipeline 12. Moreover, thanks to the fact that stationary waves occur when there is a sudden stoppage of the pig device 10 and thanks to the fact that the detection system is permanently active or, in other words, "alert", the method according to the present invention makes it possible to detect the position of the pig device 10 inside the pipeline 12 even if such a pig device 10 is blocked definitively and can no longer be restarted. The control unit 16 is indeed capable of recording and analysing a posteriori the track of the last sound signal generated by the pig device 10 before its final stoppage.

In detail, the method for detecting the position of the pig device 10 inside the pipeline 12 develops in the following manner. The vibro-acoustic sensors 14 installed in at least one of the terminals A and B of the pipeline 12 measure, continuously, the sound signals (pressure waves in the fluid) generated by the discontinuous movement of the pig device 10 during the advance and scraping phases on the welding dents between adjacent sections of tube.

Typically, a normal pipeline for gas transportation is composed of single sections that are around 10-12 meters long, welded together. The advance phases of the pig device 10 in the pipeline 12 are recognised, even at tens of kilometers away, as pressure peaks having greater amplitude with respect to the background noise caused by fluid being transported, and produced by the transit of the pig through the welding dents, every 10-12 meters.

In the time periods of the stoppage of the pig device 10, the pipeline 12 for transporting the fluid is similar, as regarding the propagation of the sound signals, to a section of closed tube and/or an acoustic guide that is strongly mismatched at its two ends. The sound signal in these time periods is analysed and processed by the control unit 16 so as to identify a possible family of harmonics (resonance frequencies) connected with the presence of stationary waves. The fundamental harmonic of each stationary wave, the propagation speed of the sound in the fluid inside the pipeline 12 being known, is univocally connected to the length of the section of the pipeline 12 being tested and therefore to the distance/position of the pig device 10 with respect to the measurement station.

The detection distance or, in other words, the maximum distance between the measurement station and the pig device 10 which makes it possible for the vibro-acoustic sensors 14 to correctly identify the position of such a pig device 10, is a function of:

attenuation of the sound signal that propagates inside the pipeline 12;

dynamic sensitivity of the vibroacoustic measurement sensors 14;

bandwidth of the acoustic measurement instrumentation.

A typical acoustic measurement instrumentation is capable of ensuring a frequency range of between 0.01 Hz and 10 Hz, more typically between 0.1 Hz and 10 Hz. With the use of acoustic measurement instrumentation of the "commercial" type, in pipes 12 with an internal diameter of around 20" (typical for long distance fluid transportation) the detection distance of the pig device 10 can reach the value of around 30 km from the measurement station. With the increase of both the diameter of the pipeline 12, and of the pressure of the fluid transported in it, also the distance of remote detection of the pig device 10 increases.

In the rest of the description we shall give an example embodiment applying the method and the system according to the present invention to an offshore gas transportation pipeline, currently in service. In particular, sound pressure signals have been collected at the arrival terminal B of the pig device 10, during a cleaning phase of the pipeline 12 with the fluid transported at low pressure (around 8 bar of pressure in the pipeline 12 and around 2 bar of differential pressure between the two front 10A and rear 10B sides of the pig device 10).

In these conditions the pig device 10 moves in a discontinuous manner in the pipeline 12, with stops of a few minutes and running for some tens of seconds. The sound pressure signal, recorded with hydrophones and measured at the arrival station B of the pig device 10, as predicted, shows the following harmonic structures (FIGS. 2A and 2B):

broad high spectral peaks, related to the restarting instances of the pig device 10 in the underwater pipeline 12;

a train of resonance harmonics with a fundamental frequency that increases as the pig device 10 comes closer to the arrival terminal B of the pipeline 12;

a useful acoustic detection distance of around 3-5 km from the arrival terminal B of the pipeline 12.

It has thus been seen that the method and the system for the remote detection of the position of a Pig device inside pipelines for transporting pressurised fluids according to the present invention achieve the purposes previously highlighted.

The method and the system for the remote detection of the position of a pig device inside pipelines of the present invention thus conceived can in any case undergo numerous modifications and variants, all covered by the same inventive concept. The scope of protection of the invention is therefore defined by the attached claims.

The invention claimed is:

1. A method for remote detection of a position of a pig device inside a pipeline configured for transporting a pressurized fluid, wherein the pig device advances in the pipeline with an intermittent movement, with alternating advance and stoppage phases, the method comprising:

detecting continuously, by a measurement station located in at least one terminal of the pipeline, sound waves generated inside the pipeline by pressure variations in the pressurized fluid which arise at a front side and/or a rear side of the pig device during the alternating advance and stoppage phases;

analyzing and processing, using a controller, stationary waves caused by reverberations inside the pipeline of the sound waves generated in time periods of the stoppage phase of the pig device;

identifying a family of resonance harmonics connected with presence of the stationary waves, a reverberation period and/or a resonance frequency of each said stationary wave, a propagation speed of the sound waves in the pressurized fluid inside the pipeline being known, being univocally connected to a length of a section of the pipeline being tested; and determining based on the reverberation period and/or the resonance frequency of each said stationary wave, a distance of the pig device with respect to the measurement station allowing calculation of the position of the pig device along the pipeline.

2. The method according to claim 1, wherein the detection phase of the sound waves generated inside the pipeline is performed by two measurement stations respectively located at a first terminal end and at a second terminal end of the pipeline.

3. The method according to claim 2, wherein the controller performs measurements of the arrival times of signals deriving from the sound waves detected by the two measurement stations.

4. The method according to claim 1, wherein the propagation speed of the sound waves in the pressurized fluid inside the pipeline is obtained using mathematical sound propagation models which take into consideration physical and geometrical characteristics of a system consisting of the pipeline, the pressurized fluid transported, and a surrounding environment of the pipeline.

5. The method according to claim 1, wherein the controller is configured to record and analyze a posteriori a track of a last signal deriving from the sound waves generated by the pig device, thus checking the position of the pig device inside the pipeline even if the pig device is blocked definitively and can no longer be restarted.

6. The method according to claim 1, wherein the pressurized fluid is transported in the pipeline with an absolute pressure ranging from about 3 bar to about 10 bar.

7. The method according to claim 1, wherein a differential pressure between the front and rear sides of the pig device ranges from about 1 bar to about 3 bar.

8. The method according to claim 1, wherein the pressurized fluid consists of natural gas.

9. A system for remote detection of a position of a pig device inside a pipeline configured for transporting a pressurized fluid, wherein the pig device advances in the pipeline with an intermittent movement, with alternating advance and stoppage phases, the system comprising:
- at least one measurement station, situated in at least one terminal of the pipeline, said measurement station comprising one or more sensors configured to continuously detect sound waves generated inside the pipeline by pressure variations in the pressurized fluid which arise at a front side and a rear side of the pig device during the alternating advance and stoppage phases; and
- a controller operatively connected to said one or more sensors, said controller being configured to
- analyze and process stationary waves caused by reverberations inside the pipeline of the sound waves generated in time periods of the stoppage phase of the pig device, said controller also being configured to identify a family of resonance harmonics connected with presence of stationary waves, wherein a reverberation period and/or resonance frequency of each said stationary wave, a propagation rate of the sound waves in the pressurized fluid inside the pipeline being known, are univocally connected to a length of a section of the pipeline being tested, and
- determine, based on the reverberation period and/or the resonance frequency of each said stationary wave, a distance of the pig device with respect to the measurement station allowing calculation of the position of the pig device along the pipeline.

10. The system according to claim 9, further comprising two measurement stations respectively located at a first terminal end and at a second terminal end of the pipeline.

11. The system according to claim 9, wherein said one or more sensors consist of hydrophones or vibroacoustic sensors.

12. The system according to claim 11, wherein said hydrophones or vibroacoustic sensors are configured to detect a frequency range from 0.01 Hz to 10 Hz.

13. The system according to claim 9, wherein said controller is operatively connected to said one or more sensors by a wired communication system.

14. The system according to claim 9, wherein said controller is operatively connected to said one or more sensors by a wireless-type communication system.

* * * * *